United States Patent
Osher et al.

(10) Patent No.: US 10,117,703 B2
(45) Date of Patent: Nov. 6, 2018

(54) METHOD OF, AND DEVICE FOR, MARKING A PATIENTS EYE FOR REFERENCE DURING A TORIC LENS IMPLANTATION PROCEDURE

(71) Applicant: BEAVER-VISITEC INTERNATIONAL (US), INC., Lake Forest, IL (US)

(72) Inventors: Robert H. Osher, Cincinnati, OH (US); Collin Alexander Murray, Belmont, MA (US)

(73) Assignee: BEAVER-VISITEC INTERNATIONAL (US), INC., Waltham, MA (US)

(*) Notice: Subject to any disclaimer, the term of this patent is extended or adjusted under 35 U.S.C. 154(b) by 316 days.

(21) Appl. No.: 13/653,828

(22) Filed: Oct. 17, 2012

(65) Prior Publication Data
US 2013/0096547 A1  Apr. 18, 2013

Related U.S. Application Data

(60) Provisional application No. 61/547,877, filed on Oct. 17, 2011.

(51) Int. Cl.
*A61B 18/14* (2006.01)
*A61F 9/007* (2006.01)
*A61F 2/16* (2006.01)

(52) U.S. Cl.
CPC ...... *A61B 18/1402* (2013.01); *A61B 18/1477* (2013.01); *A61F 9/007* (2013.01);
(Continued)

(58) Field of Classification Search
CPC .... A61B 2018/1422; A61B 2018/1432; A61B 19/54; A61F 9/0136
(Continued)

(56) References Cited

U.S. PATENT DOCUMENTS 4,911,161 A * 3/1990 Schechter .............. 606/107
5,342,357 A * 8/1994 Nardella ............ A61B 18/1206
606/38

(Continued)

FOREIGN PATENT DOCUMENTS

WO  02056805 A2  7/2002

OTHER PUBLICATIONS

Beaver-Visitec International Inc., Wet-Field Eraser Precise Targeted Coagulation, 2010, p. 2.*

(Continued)

*Primary Examiner* — Michael Peffley
*Assistant Examiner* — Yasamin Ekrami
(74) *Attorney, Agent, or Firm* — Budzyn IP Law, LLC

(57) ABSTRACT

In one aspect, a method is provided herein of marking a patient's eye for reference during a toric lens implantation procedure. The method includes providing an electrocautery device having a handle, a shaft extending from the handle, and a tip defined at the terminus of the shaft. The handle is elongated and extends along a longitudinal axis with the shaft being bent or curved such that the tip is spaced from, and not aligned with, the longitudinal axis. The method further includes using the electrocautery device to cauterize one or more points on the patient's eye, the points being located as reference marks for placement of the toric lens. Advantageously, with the subject invention, a device is used having a bent or curved shaft which may better accommodate the curvature of a patient's eye while marking.

2 Claims, 4 Drawing Sheets

(52) U.S. Cl.
CPC ............... *A61B 2018/1422* (2013.01); *A61B 2018/1432* (2013.01); *A61F 2/1645* (2015.04)

(58) Field of Classification Search
USPC .............................................. 606/41, 45–50
See application file for complete search history.

(56) References Cited

U.S. PATENT DOCUMENTS

| | | | | |
|---|---|---|---|---|
| 5,445,142 | A * | 8/1995 | Hassler, Jr. ........ | A61B 1/00087 600/105 |
| 5,951,546 | A * | 9/1999 | Lorentzen .......... | A61B 18/1477 606/41 |
| 6,017,340 | A * | 1/2000 | Cassidy et al. ................. | 606/47 |
| 6,428,502 | B1 * | 8/2002 | Lang ................... | A61F 9/00772 604/264 |
| 6,920,883 | B2 * | 7/2005 | Bessette et al. .............. | 128/898 |
| 6,925,333 | B2 * | 8/2005 | Krebs ................. | A61N 1/0551 606/41 |
| 7,070,596 | B1 * | 7/2006 | Woloszko et al. .............. | 606/41 |
| 7,862,563 | B1 * | 1/2011 | Cosman ............. | A61B 18/1477 606/41 |
| 2002/0111608 | A1 * | 8/2002 | Baerveldt ........... | A61F 9/00781 606/6 |
| 2007/0088352 | A1 | 4/2007 | Rosen | |
| 2008/0015565 | A1 * | 1/2008 | Davison .......................... | 606/37 |
| 2008/0086160 | A1 * | 4/2008 | Mastri ................ | A61B 17/3417 606/185 |
| 2010/0076428 | A1 * | 3/2010 | Durgin et al. .................. | 606/48 |

OTHER PUBLICATIONS

Beaver-Visitec International; XP-055049674; "Wet-Field Eraser"; Nov. 1, 2010; pp. 1-4; Waltham, MA, USA.

Robert H. Osher, MD. et al.; "Marking the Axis for a Toric IOL"; Mar. 2009; pp. 37-38. USA.

Robert H. Osher, MD.; "Iris fingerprinting: New method of improving accuracy in toric lens orientation"; Cataract Refractive Surgery Today; vol. 36, Feb. 2010, pp. 351-352; USA.

\* cited by examiner

METHOD OF, AND DEVICE FOR, MARKING A PATIENTS EYE FOR REFERENCE DURING A TORIC LENS IMPLANTATION PROCEDURE

CROSS-REFERENCE TO RELATED APPLICATION

This application claims priority to U.S. Provisional Patent Application No. 61/547,877, filed Oct. 17, 2011, the entire contents of which are incorporated by reference herein.

FIELD OF THE INVENTION

A method, and device, are provided herein useable for marking a patient's eye for reference during a toric lens implantation procedure.

BACKGROUND OF THE INVENTION

Toric lens implantation is known in the art to replace the natural lens of the eye. A toric lens is a replacement intraocular lens (TOL) used for cataract patients with pre-existing astigmatism. The correct angular position of a toric lens is a critical component in order to maximize the amount of astigmatic correction. To assist in proper placement, at least one reference mark is made on the eye, preferably on or near the limbus, to define a horizontal reference axis. Using the reference mark(s), alignment mark(s) are subsequently prepared to properly align the toric lens. In one technique, an astigmatic degree gauge (e.g., Mendez-style astigmatic degree gauge) may be utilized to locate, and permit marking of, the steep axis of astigmatism. Alternatively, the steep axis may be marked using a marker that combines an astigmatic degree gauge with an inner bezel that marks the steep axis.

Commonly, a surgical marking pen is used to make the reference marks. However, the thickness of the marker adds error and the ink of the mark is likely to diffuse, fade or disappear as it mixes with the tears from the patient's eye. Every degree of inaccuracy in the placement of a toric lens reduces the amount of cylindrical correction by approximately three percent. Thus, inaccurate or fading reference marks may present difficulties in achieving the most accurate placement of the toric lens.

One of the inventors herein has utilized a technique in which an electrocautery device, with a straight shaft and an included tip angle of 30°, has been utilized to cauterize one or more reference marks during a toric lens implantation procedure. The points of cauterization provide fixed reference marks which are not susceptible to fading or other dissipation by the patient's tears. The straightness of the shaft of the electrocautery device, however, may be cumbersome for some due to the roundness of the patient's eye. With cauterization, sufficiently good contact must be generated between the device and the target location. The angle of inclination of the device relative to the patient's eye is thus critical. Because of the straightness of the shaft, the device may be difficult to handle during marking.

SUMMARY OF THE INVENTION

In one aspect, a method is provided herein of marking a patient's eye for reference during a toric lens implantation procedure. The method includes providing an electrocautery device having a handle, a shaft extending from the handle, and a tip defined at the terminus of the shaft. The handle is elongated and extends along a longitudinal axis with the shaft being bent or curved such that the tip is spaced from, and not aligned with, the longitudinal axis. The method further includes using the electrocautery device to cauterize one or more points on the patient's eye, the points being located as reference marks for placement of the toric lens. Advantageously, with the subject invention, a device is used having a bent or curved shaft which may better accommodate the curvature of a patient's eye while marking. The subject invention also covers the device useable in the method described herein.

In a further aspect, an electrocautery device is provided having a shaft gauge in the range of 23-27 with an included tip angle in the range of 60°-180°, more preferably, 60°-150°, and more preferably 60°-120°, Forming an included tip angle in accordance with the subject invention allows for smaller, minimally eccentric reference marks to be made during a procedure. The included tip angle range of the subject invention provides an advantage for both straight-shaft and bent/curved shaft electrocautery devices.

These and other features of the invention will be better understood through a study of the following detailed description and accompanying drawings.

DETAILED DESCRIPTION OF THE INVENTION

Figure 1:
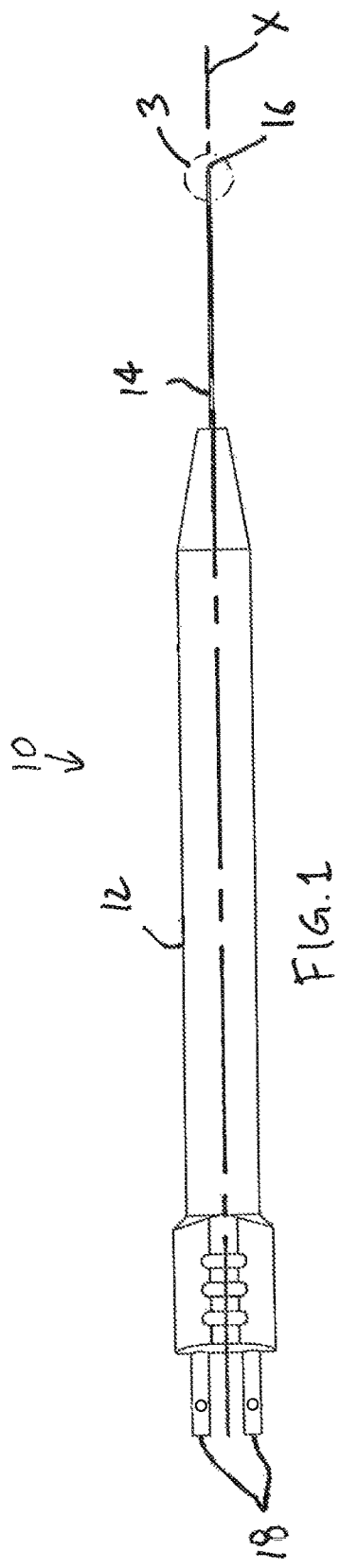
FIG. 1 is a top plan view of a device formed in accordance with the subject invention.

With reference to the figures, an electrocautery device 10 is shown which generally includes a handle 12, a shaft 14 extending from the handle 12, and a tip 16 defined at the terminus of the shaft 14. The device 10 is particularly well-suited for use during a toric lens implantation procedure, as described herein, but may have application elsewhere, as will be appreciated by those skilled in the art.

The device 10 is configured to cauterize tissue upon sufficient contact with the tip 16. Various electrocautery devices are known in the art including devices sold under the tradename "WET-FIELD® ERASER®" by Beaver-Visitec International, Inc. of Waltham, Mass. The device 10 may, be provided with bipolar diathermy capability, or other features. The shaft 14, including the tip 16, may be provided in various gauges, but preferably a smaller-diameter gauge is provided, such as a 20-27 gauge, more preferably, a 23-25 gauge, and even more preferably, a 25 gauge design is provided. The tip 16 may be tapered to include tip angle β so as to further reduce the diameter thereabout.

The device 10 may include one or more electrical contacts 18 for electrically coupling to a source of electricity. As is known in the prior art, the device 10 is configured such that electrical flow is delivered to the tip 16 such that upon contact with the tissue, energy is generated for hemostasis. The tip 16, as is known in the art, may be comprised of three layers (these layers being exposed at the tip 16): an outer the 16a; an inner conductive wire 16b; and, an insulation layer 16c between the outer tube 16a and the inner conductive wire 16b. In use, electricity is caused to flow between the inner conductive wire 16b and the outer the 16a through tissue in contact with the tip 16. Any known configuration for generating energy for hemostasis may be used.

The handle 12 is formed of an insulative material so as to protect a user from exposure to electrical flow through the device 10. Preferably, the exposed portions of the shaft 14 are also electrically insulated from the flow of electricity.

Figure 2:
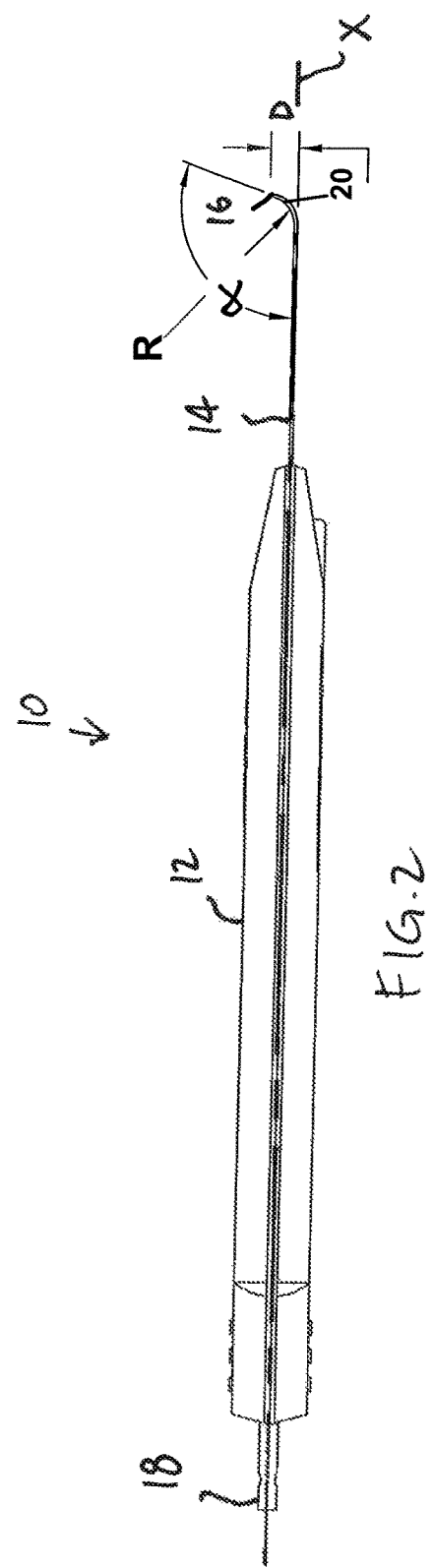
FIG. 2 is a side elevational view of a device formed in accordance with the subject invention.
Figure 4:
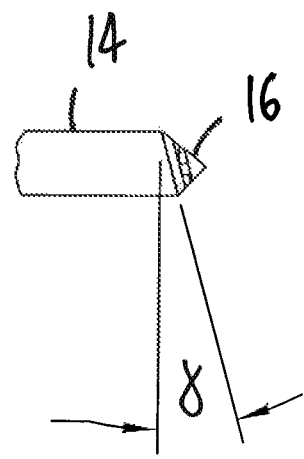
FIG. 4 shows a tip useable with the subject invention.
Figure 5:
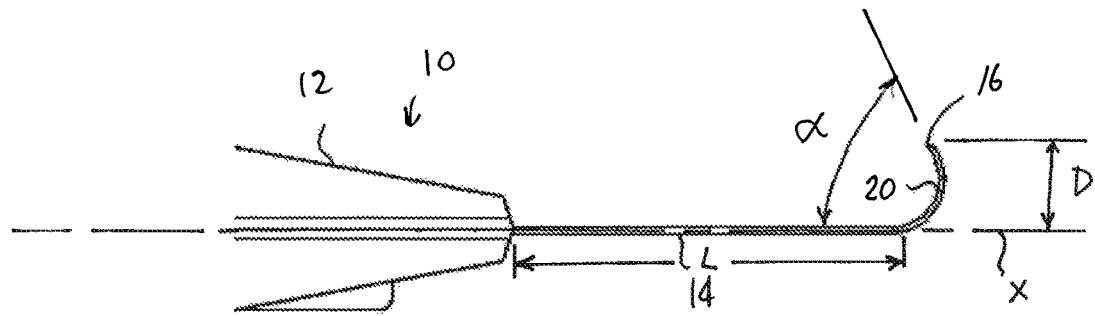
FIGS. 5-7 show different shaft configurations useable with the subject invention.
Figure 6:
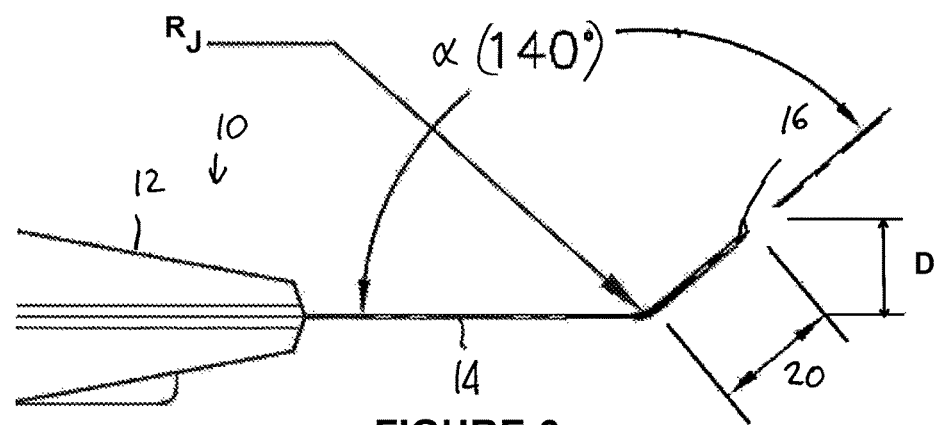
Figure 7:
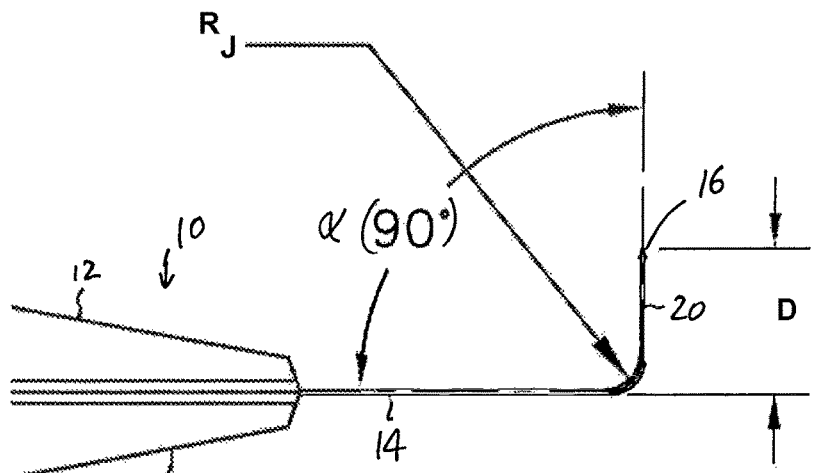

As shown in FIG. 1, the handle 12 is elongated and formed to extend along a longitudinal axis X. A portion of the shaft 14 coincides with the longitudinal axis X. In addition, the shaft 14 is bent or curved such that the tip 16 is spaced from, and not aligned with, the longitudinal axis X. This provides the shaft 14 with a length 20 extending between the longitudinal axis X and the tip 16. Preferably, the length 20 is arcuate between the tip 16 and the longitudinal axis X, as shown in FIGS. 2 and 5. With the length 20 being arcuate, the length 20 may be formed about a radius R. Alternatively, FIGS. 6 and 7 show the length 20 being generally straight. With the length 20 being generally straight, it is preferred that the length 20 extend from the shaft 14 about a joint having a joint radius $R_J$ (FIGS. 6 and 7). The length 20 may be composed of a combination of arcuate and straight portions. It is preferred that the shaft 14 have a length L between the handle 12 and the length 20 in the range of 0.5-1.5 inches. As shown in FIG. 4, the junction between the shaft 14 and the tip 16 is disposed along junction angle γ, which may be in the range of 0° to 15° relative to a reference axis perpendicular to the longitudinal axis X.

It is also preferred that the tip 16 be located a distance D away from the longitudinal axis X which is preferably in the range of 0.125-0.25 inches. Depending on the configuration of the length 20, the length 20 may equal the distance D. Further, it is preferred that the length 20, as oriented at the tip 16, subtend an approximately right or greater angle α relative to the longitudinal axis X as measured between the length 20 and the rest of the shaft 14. It is preferred that the angle α be in the range of 90°-140°, it is most preferred for the angle α to be approximately 90 degrees. The angle α may be acute, but, if acute, preferably, the angle α is a large acute angle (60 degrees or greater).

Figure 8:
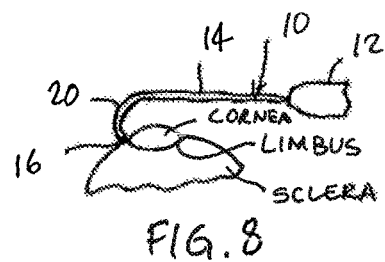
FIG. 8 is a schematic showing a device formed in accordance with the subject invention in use.
Figure 9:
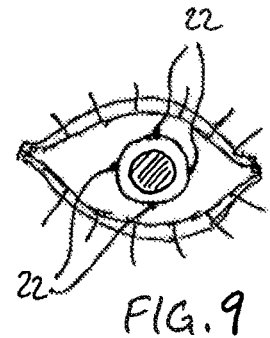
FIG. 9 is a schematic showing reference mails performed by the subject invention.

With reference to FIG. 8, the bent or curved portion of the shaft 14 allows for the shaft 14 to extend across a curved portion of a patient's eye without interference therefrom with the tip 16 in contact with a target location. Preferably, the tip 16 is in full point contact at the target location. With reference to FIG. 9, with the device 10, one or more points of cauterization 22 may be formed on the eye with the device 10 to define one or more reference marks, particularly for defining a reference axis for alignment of a toric lens. It is preferred that the points of cauterization 22 be formed on or near the limbus.

Figure 3:
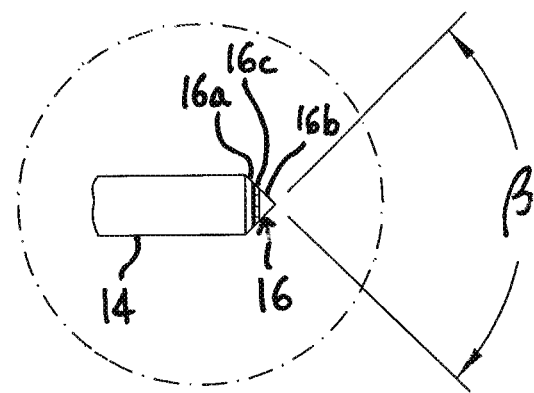
FIG. 3 is an enlarged view of Section 3 of FIG. 1.

With reference to FIG. 3, it is preferred that with the shaft 14 being provided with a gauge of 23-27, more preferably, a 25-27 gauge, and even more preferably, a 25 gauge, the tip angle β be in the range of 60°-180°, more preferably in the range of 60°-150°, and more preferably in the range of 60°-120°, The shaft 14 may be bent or curved as described above, or may be straight (i.e., the angle α being 180°). A device as described here may be used in applications other than toric lens implantation.

Figure 10:
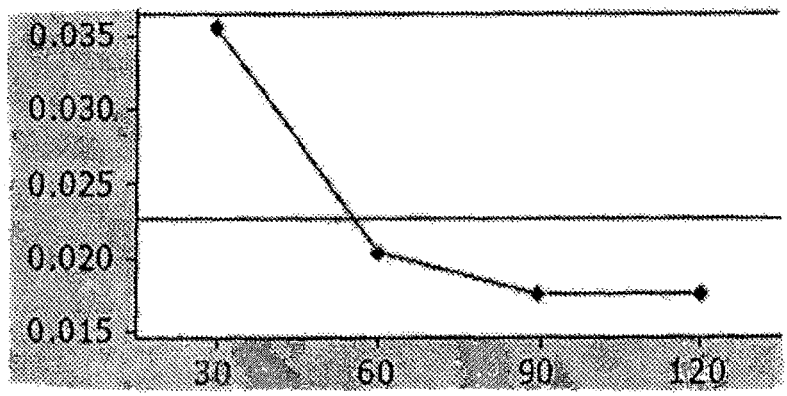
FIGS. 10-11 are plots showing reference mark diameter and eccentricity achievable with the subject invention.
Figure 11:
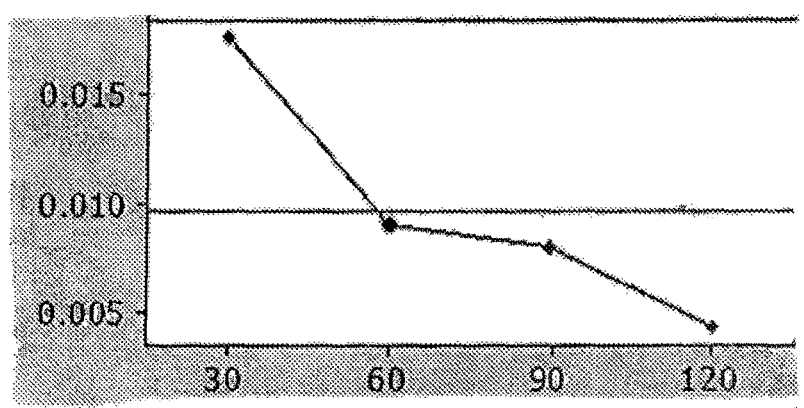

With reference to FIGS. 10 and 11, tests were conducted using porcine eyeballs to evaluate the performance of the tip angle β relative to the prior art. With these tests, electrocautery devices (having a 25 gauge) were prepared having all the same characteristics (gauge, electrical input, etc.) except for the included tip angle. As shown in FIG. 10, it has been found that the tip angle β formed in accordance with the subject invention provides for formation of a smaller reference mark (FIG. 10), as measured by the diameter of the reference mark, than achievable with a prior art tip design (tip angle of 30°). Also, as shown in FIG. 11, it has been found that the tip angle β formed in accordance with the subject invention provides for less eccentricity in a generated reference mark as compared with reference marks generated by a prior art tip design (tip angle of 30°). Less eccentricity indicates greater circularity (eccentricity of 0.000 indicates complete circularity (no eccentricity)). The formation of visible, smaller, minimally-eccentric reference marks is highly desirable and achievable with the subject invention. Such reference marks provide clearer indication of location. Greater variability in surgery exists with larger, eccentric reference marks with a tip angle of 30°. Variation in the reference marks may undesirably result in improper location of the marking of the steep axis of astigmatism.

What is claimed is:

1. An electrocautery device for marking a patient's eye, the device comprising:
   a handle;
   a shaft extending from said handle, said shaft having a gauge in the range of 25-27; and,
   a conical tip defined at a terminus of said shaft,
   wherein, said conical tip being tapered so as to include a tip angle in the range of 60°-120° for forming one or more points of cauterization on the patient's eye, a vertex of said tip angle being centrally located relative to a cross-section of said shaft, and
   wherein, said conical tip including an exposed inner conductive wire coinciding with said vertex of said tip angle, an outer tube, and an exposed insulation layer between said inner conductive wire and said outer tube.

2. An electrocautery device as in claim 1, wherein said gauge is 25.

* * * * *